US012333076B2

(12) United States Patent
Lee et al.

(10) Patent No.: US 12,333,076 B2
(45) Date of Patent: Jun. 17, 2025

(54) VIRTUAL TACTILE STIMULATION DEVICE AND METHOD FOR MATCHING NERVE STIMULATION PATTERN AND VIRTUAL SPACE OBJECT HAVING IMPEDANCE

(71) Applicant: Electronics and Telecommunications Research Institute, Daejeon (KR)

(72) Inventors: Sung Q Lee, Daejeon (KR); Kang Ho Park, Daejeon (KR); You Sung Kang, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 110 days.

(21) Appl. No.: 18/304,148

(22) Filed: Apr. 20, 2023

(65) Prior Publication Data
US 2023/0341942 A1 Oct. 26, 2023

(30) Foreign Application Priority Data
Apr. 21, 2022 (KR) .................. 10-2022-0049351

(51) Int. Cl.
G06F 3/01 (2006.01)
A61N 1/36 (2006.01)
(Continued)

(52) U.S. Cl.
CPC .......... G06F 3/016 (2013.01); A61N 1/3606 (2013.01); A61N 1/3614 (2017.08); G06F 3/011 (2013.01);
(Continued)

(58) Field of Classification Search
CPC .......... G06F 3/016; G06F 3/015; G06F 3/014; G06F 3/011; G06T 17/00; A61N 1/0456; A61N 1/3606; A61N 1/3614
See application file for complete search history.

(56) References Cited

U.S. PATENT DOCUMENTS 9,882,724 B2    1/2018  Hyun et al.
2016/0274662 A1* 9/2016  Rimon ...................... G06F 3/16
(Continued)

FOREIGN PATENT DOCUMENTS

CN    109804331 A * 5/2019 ........... G06F 3/0236
KR    10-2011-0016385    2/2011
(Continued)

OTHER PUBLICATIONS

"Prosthesis with neuromorphic multilayered e-dermis perceives touch and pain", Osborn et al, 2018.
(Continued)

Primary Examiner — Adam J Snyder
(74) Attorney, Agent, or Firm — KILE PARK REED & HOUTTEMAN PLLC

(57) ABSTRACT

The present disclosure relates to a tactile emotion recognition method and device, and is directed to assigning an impedance value to each object in a virtual space; inducing virtual force using displacement between the object and a user's body in the virtual space; inducing a signal, which causes a signal of a sensory nerve to be fired, with a value corresponding to the virtual force; stimulating a location where the sensory nerve is located temporarily or over time; and generating feedback in the virtual space based on a stimulation result.

18 Claims, 14 Drawing Sheets

(51) Int. Cl.
*G06T 17/00* (2006.01)
*A61N 1/04* (2006.01)

(52) U.S. Cl.
CPC ............ *G06T 17/00* (2013.01); *A61N 1/0456* (2013.01); *G06F 3/014* (2013.01); *G06F 3/015* (2013.01)

(56) References Cited

U.S. PATENT DOCUMENTS

| | | |
|---|---|---|
| 2018/0019877 A1 | 1/2018 | Koo |
| 2020/0218338 A1* | 7/2020 | Lee ........................ G06F 3/013 |
| 2020/0393905 A1* | 12/2020 | Daniels ................. G06F 1/1694 |
| 2025/0040864 A1 | 2/2025 | Ang et al. |

FOREIGN PATENT DOCUMENTS

| | | |
|---|---|---|
| KR | 10-2019-0041467 | 4/2019 |
| KR | 10-2188851 | 12/2020 |
| KR | 10-2245898 | 4/2021 |

OTHER PUBLICATIONS

"Dynamic Spatiotemporal Pattern Identification and Analysis Using a Fingertip-based Electro-Tactile Display Array", Rahimi et al, 2019.
"Design of Electro-tactile Stimulation to Represent Distribution of Force Vectors", Sato et al, 2010.
"Electro-tactile display composed of two dimensionally and densely distributed microneedle electrodes", Tezuka et al, 2017.

\* cited by examiner

VIRTUAL TACTILE STIMULATION DEVICE AND METHOD FOR MATCHING NERVE STIMULATION PATTERN AND VIRTUAL SPACE OBJECT HAVING IMPEDANCE

CROSS-REFERENCE TO RELATED APPLICATION

This application claims priority to and the benefit of Korean Patent Application No. 10-2022-0049351, filed on Apr. 21, 2022, the disclosure of which is incorporated herein by reference in its entirety.

BACKGROUND

1. Field of the Invention

The present disclosure relates to a tactile stimulation device and a method thereof, and specifically, to technology for a virtual tactile stimulation device and a method for matching a nerve stimulation pattern and impedances of virtual space objects.

2. Discussion of Related Art

Humans exchange information with the outside world through their sensations. The existing sensory organs of sight and hearing have innovatively changed and developed human life, and are more information is expected to be transmitted and received through extension to other sensations. In particular, haptic technology that implements a tactile sensation or tactile encoding technology that enables the tactile sensation to be detected will further advance human life.

In the recent post-corona era, the "untact" era has arrived, and due to leaps in metaverse technology, technology that enables natural communication between people in a virtual space is required. Along with sight and hearing, haptic technology and artificial tactile realization technology will become essential elements. In contrast to these social demands, tactile realization technology is still limited. Currently, various technologies including wearable tactile realization technology such as haptic gloves or suits implementing a virtual tactile sensation or contact/non-contact tactile realization technology such as electricity, ultrasonic waves, and light have been introduced, but these technologies etc., are inconvenient in terms of utility, and since there are many technologies that are not based on tactile nerve spike technology, actual sensitivity is low. In order to realize a more realistic tactile sensation, there is a need for a technology of encoding a tactile sensation in a sensory receptor through a stimulation device using electricity or ultrasonic waves and transmitting the encoded tactile sensation to a central nervous system. However, due to insufficient research on a coding model on how a tactile sensation is coded in a nerve signal, it is still difficult to implement technology that presents various tactile sensations.

Among the related arts, US Patent No. 1 (US2020/0393905A1, John, J. Daniel, Wearable electric haptic feedback system for VR/AR and Gaming) suggests a device for providing a tactile sensation through electrical stimulation in a virtual space. It presents a system for providing haptic feedback, an electrode arrangement and structure, and a structure of a wearable haptic system, and also introduces sensor systems for measuring pressure, position, and acceleration.

In the case of the related art, there is no method of deriving a force or tactile sensation to be felt in a virtual space, there is no method of a stimulation pattern that stimulates a nerve, it is not possible to implement electrical stimulation to individually feel pressure and vibration in the entire two-dimensional array, it is difficult to implement technology for applying electrical stimulation to the Pacinian corpuscle that feels fast and strong vibration, and since electricity is applied outside a stratum corneum, the applied voltage is more than several tens of volts and it is difficult to actually implement the electrical stimulation, which is uncomfortable for a user.

SUMMARY OF THE INVENTION

The present disclosure is directed to providing a tactile stimulation method and a tactile stimulation device capable of deriving virtual force using a relative distance between a boundary and a hand feeling tactile sensation and an impedance assigned to an object with a virtual boundary at a certain distance from an object in a virtual space, and generating feedback on the virtual force by an electrical stimulation method using a sensory receptor nerve model.

Other objects and advantages of the present disclosure may be understood from the following description and will be more clearly appreciated with reference to embodiments of the present disclosure. In addition, it may be easily appreciated that objects and advantages of the present disclosure may be realized by means disclosed in the claims and combinations thereof.

According to an aspect of the present invention, there is provided a tactile stimulation method, including: assigning an impedance value to each object in a virtual space; inducing virtual force using displacement between the object and a user's body in the virtual space; inducing a signal, which causes a signal of a sensory nerve to be fired, with a value corresponding to the virtual force; stimulating a location where the sensory nerve is located through a nerve stimulation unit temporarily or over time; and generating feedback in the virtual space based on a stimulation result.

The assigning of the impedance value to each object in the virtual space includes assigning a different representative impedance value according to contact strength of the object in the virtual space.

The spike signal may acquire spike pattern data acquired from the sensory nerve by applying a mechanical force, and may be generated using a spike signal of a correlation function based on the acquired spike pattern data.

The correlation functions may include a functions that model resistance-capacity (RC) discharging responses.

The tactile stimulation method may further include stimulating the nerve by applying any one of electrical signals including a constant magnitude of current, a spike, and a pulse pattern that fire the nerve.

The tactile stimulation method may further include stimulating a stimulation array corresponding to an individual sensory nerve with a spike according to movement of the body in the virtual space so that the feedback is felt in the virtual space.

The tactile stimulation method may further include: applying an individual electrical signal from an individual electrode; adjusting a bioelectrical impedance between the individual electrode and skin manipulation; adjusting a depth at which an electrical spike or a pulse signal is applied on a skin surface based on the adjusted bioelectrical impedance; and performing stimulation so that the feedback is felt by distinguishing a tactile sensory nerve receptor based on the adjusted depth.

The tactile stimulation method may further include adjusting a frequency of the electrical signal to adjust the bioelectrical impedance between the individual electrode and the skin manipulation.

The tactile stimulation method may further include adjusting the bioelectrical impedance between the individual electrode and the skin manipulation by changing at least one of a width and a length of the individual electrode.

The tactile stimulation method may further include adjusting the bioelectrical impedance between the individual electrode and the skin manipulation using an impedance matching film applied on the individual electrode.

According to another aspect of the present invention, there is provided a tactile stimulation device, including: an impedance assigning unit configured to assign an impedance value to each object in a virtual space; virtual force induction unit configured to induce virtual force using displacement between the object and a user's body in the virtual space; a signal induction unit configured to induce a signal, which causes a signal of a sensory nerve to be fired, with a value corresponding to the virtual force; a nerve stimulation unit configured to stimulate a location where the sensory nerve is located temporarily or over time; and a feedback generation unit configured to generate feedback in the virtual space based on a stimulation result.

The impedance assigning unit may assign a representative impedance value differently according to contact strength of the object in the virtual space.

The spike signal may acquire spike pattern data acquired from the sensory nerve by applying a mechanical force, and may be generated using a spike signal of a correlation function based on the acquired spike pattern data.

The correlation functions may include a functions that model resistance-capacity (RC) discharging responses.

The nerve stimulation unit may stimulate the nerve by applying any one of electrical signals including a constant magnitude of current, a spike, and a pulse pattern that fire the nerve.

The nerve stimulation unit may stimulate a stimulation array corresponding to an individual sensory nerve with a spike according to movement of the body in the virtual space so that the feedback is felt in the virtual space.

The nerve stimulation unit may apply an individual electrical signal from an individual electrode, adjust a bioelectrical impedance between the individual electrode and skin manipulation, adjust a depth at which an electrical spike or a pulse signal is applied on a skin surface based on the adjusted bioelectrical impedance, and perform stimulation so that the feedback is felt by distinguishing a tactile sensory nerve receptor based on the adjusted depth.

The nerve stimulation unit may adjust a frequency of the electrical signal to adjust the bioelectrical impedance between the individual electrode and the skin manipulation.

The nerve stimulation unit may adjust the bioelectrical impedance between the individual electrode and the skin manipulation by changing at least one of a width and a length of the individual electrode.

According to still another aspect of the present invention, there is provided a tactile stimulus recognition device, including: a transceiver configured to transmit and receive data to and from an external device; and a processor configured to assign an impedance value to each object in a virtual space through the transceiver, induce virtual force using displacement between the object and a user's body in the virtual space, induce a signal, which causes a signal of a sensory nerve to be fired, with a value corresponding to the virtual force, stimulate a location where the sensory nerve is located temporally or over time, and generate the feedback in the virtual space based on a stimulation result.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
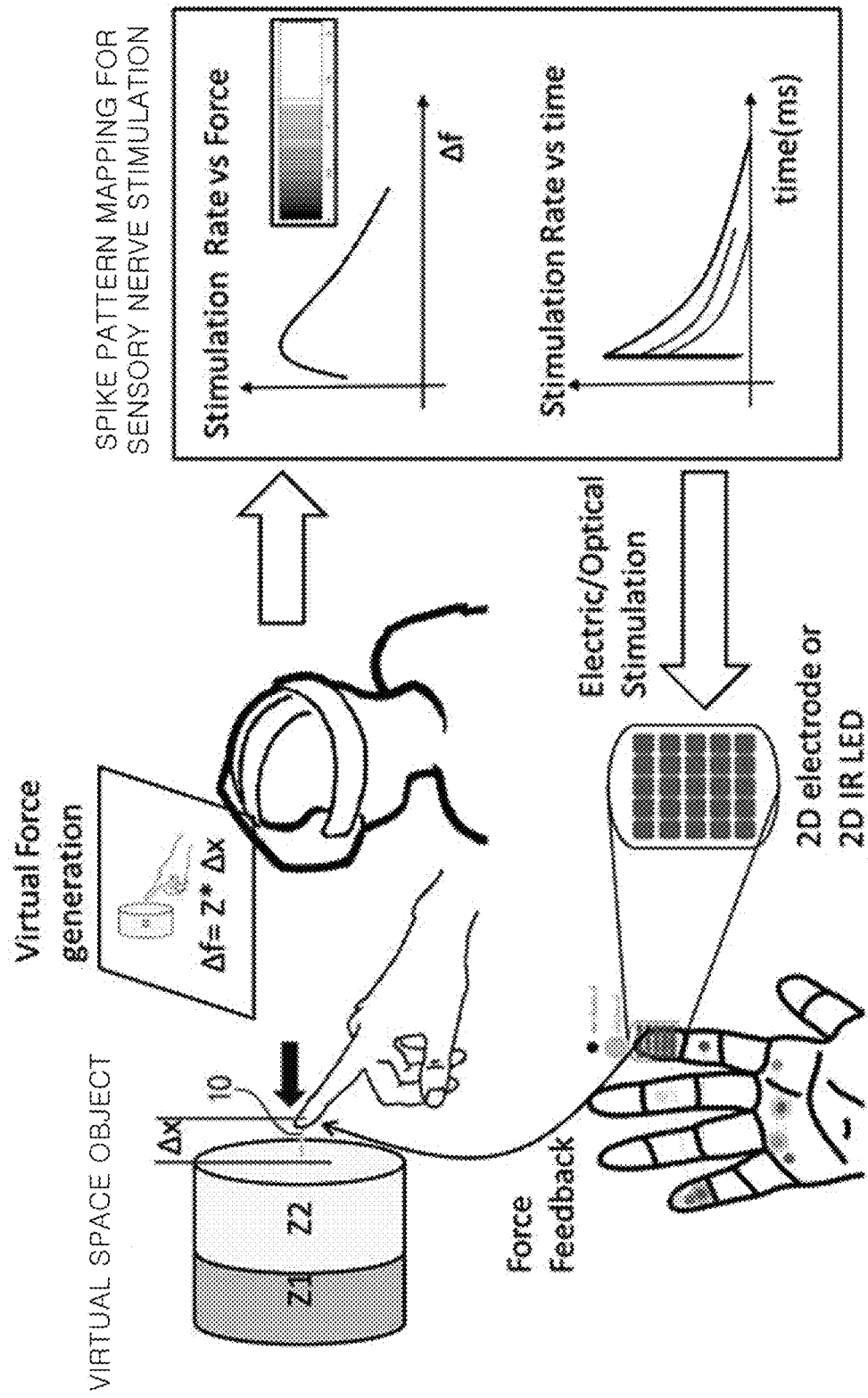
FIG. 1 is a diagram illustrating a concept of the present invention according to an embodiment of the present disclosure.

Hereinafter, embodiments of the present disclosure will be described in detail with reference to the accompanying drawings so that those skilled in the art to which the present disclosure pertains may easily practice the present disclosure. However, the present disclosure may be modified in various different forms, and is not limited to embodiments described herein.

Further, in describing exemplary embodiments of the present disclosure, well-known functions or constructions will not be described in detail since they may unnecessarily obscure the understanding of the present disclosure. In the drawings, parts not related to the description of the present disclosure are omitted, and similar reference numerals are attached to similar parts.

In the present disclosure, components distinguished from each other are intended to clearly explain each feature, and do not mean that the components are necessarily separated. That is, a plurality of components may be integrated to be formed in a single hardware or software unit, or a single component may be distributed to be formed in a plurality of hardware or software units. Accordingly, even if not described separately, even such integrated or distributed embodiments are included in the scope of the present disclosure.

In the present disclosure, components described in various embodiments are not necessarily essential components, and some of the components may be optional components. Therefore, embodiments composed of a subset of components described in an embodiment are also included in the scope of the present disclosure. In addition, embodiments including other components in addition to the components described in various embodiments are also included in the scope of the present disclosure.

In the present disclosure, terms such as "first" and "second" are used only for the purpose of distinguishing one component from other components, and do not limit the order, importance, or the like of components unless otherwise specified. Accordingly, within the scope of the present disclosure, a first component in an embodiment may be referred to as a second component in another embodiment, and similarly, a second component in an embodiment may be referred to as a first component in other embodiments.

It is to be understood that when one element is referred to as being "connected to" or "coupled to" another element, it may be connected directly to or coupled directly to another element or may be connected to or coupled to another element with still another element intervening therebetween. On the other hand, it is to be understood that when one component is referred to as being "connected directly to" or "coupled directly to" another component, it is connected to or coupled to another component with no other component interposed therebetween.

In addition, in the present disclosure, the description of each drawing may be applied to different drawings unless one drawing illustrating an embodiment of the present disclosure corresponds to another drawing and an alternative embodiment.

Hereinafter, the present disclosure will be described in more detail with reference to the drawings.

FIG. 1 is a diagram illustrating a concept of the present invention according to an embodiment of the present disclosure.

Specifically, FIG. 1 is a conceptual diagram illustrating a series of operations of obtaining virtual force through a relative distance between a sensing unit and a virtual object in a virtual space when relative displacement occurs in a vertical or horizontal direction with respect to an object located in the virtual space in the virtual space, deriving a nerve spike rate pattern for sensory nerve stimulation in order to implement the obtained virtual force, and stimulating nerves of a user through electricity, ultrasonic waves, and light energy using the nerve spike rate pattern.

Referring to FIG. 1, the relative displacement occurs in a vertical or horizontal direction with respect to an object located in a virtual space by a user. In this case, in order to provide tactile information in the virtual space, a magnitude of force to be expressed by assigning an impedance to the object in the virtual space and obtaining a relative distance 10 between a user's body feeling a tactile sensation and a virtual object in the virtual space based on the assigned impedance is derived by a number of operations. Here, the user's body may be a hand or a finger.

Here, the impedance of the object is a mechanical impedance and may be expressed using a spring constant k and a damping coefficient d.

Virtual force $\Delta f$ obtained according to a direction and value of a relative distance $\Delta x$ between the virtual object and the user's body may be expressed by Equations 1 and 2 below.

$$\Delta f = k^* \Delta x + d^* \Delta \dot{x} \qquad \text{[Equation 1]}$$

$$\Delta f^* = Z^* \Delta x \qquad \text{[Equation 2]}$$

Spike pattern mapping for sensory nerve stimulation is performed using the virtual force. Prior to the spike pattern mapping for the sensory nerve stimulation, the corresponding model is formed based on the results of spike signals fired from sensory receptors when sensory nerves are mechanically stimulated.

In the present invention, modeling is performed using a resistance-capacitance (RC) model. Specifically, when the RC model is acquired, a spike pattern for stimulation that implements virtual force is generated through an inverse model of the RC model. Using the generated spike pattern, the sensory nerve is stimulated through any one of electrical stimulation, ultrasonic stimulation, and infrared energy stimulation. In this case, the tactile information derived from the virtual space is transmitted to the actual sensory nerve, and thus a user may feel feedback.

Figure 2A:
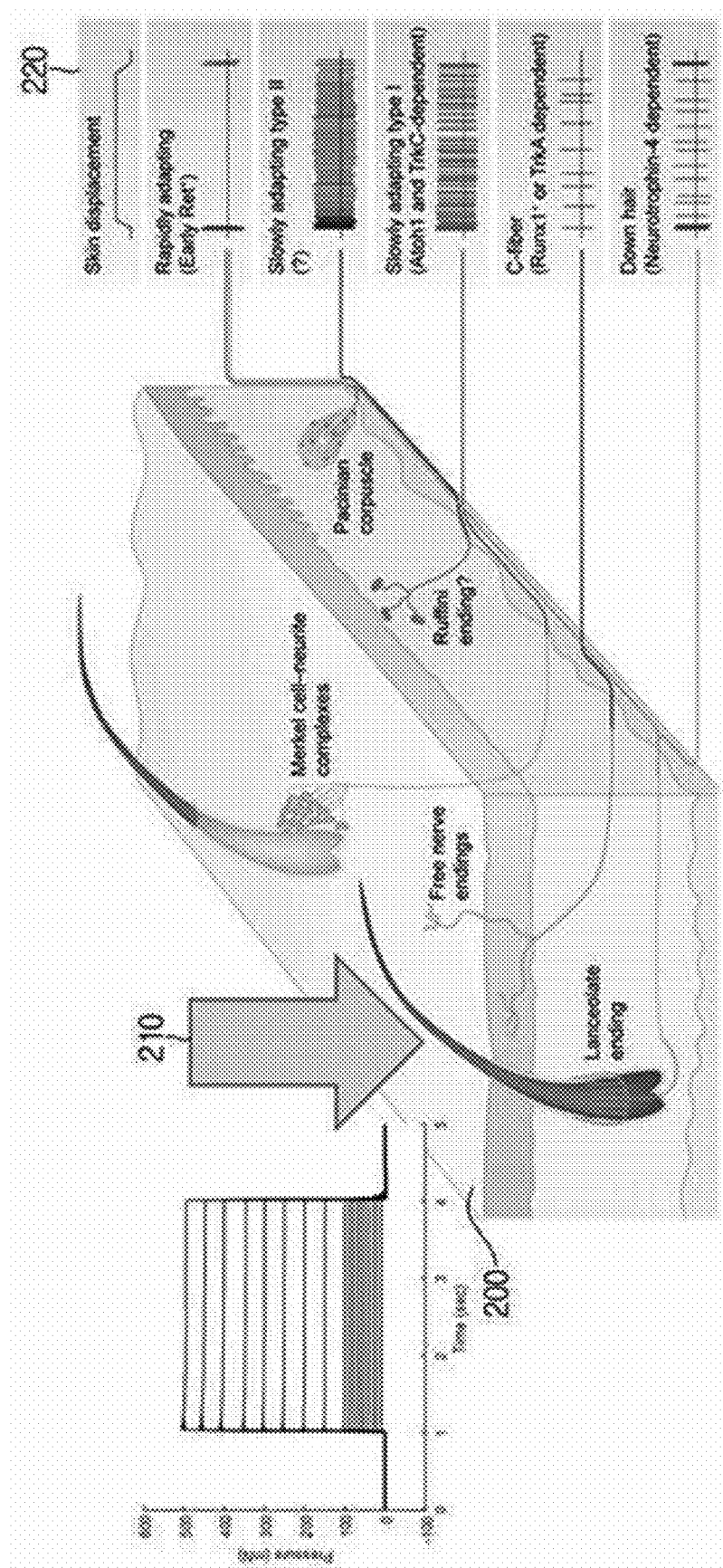
FIG. 2A is a diagram illustrating tactile nerve modeling according to an embodiment of the present disclosure.

FIG. 2A is a diagram illustrating tactile nerve modeling according to an embodiment of the present disclosure.

Referring to FIG. 2A, when mechanical stimulation 210 is applied to a skin layer 200 in which tactile nerves are distributed, an appearance in which a spike pattern 220 is fired in various sensory receptors in the skin layer 200 may be seen. Here, the sensory receptors include Pacinian, Ruffini, and Merkel receptors.

When the mechanical stimulation 210 is applied to the skin layer 200 in which the tactile nerves are distributed, the spike pattern 220 is fired in various sensory receptors in the skin layer 200.

A nerve spike rate may be obtained by obtaining an inter-spike interval (ISI) of the fired spike and taking a reciprocal of the obtained value.

Figure 2B:
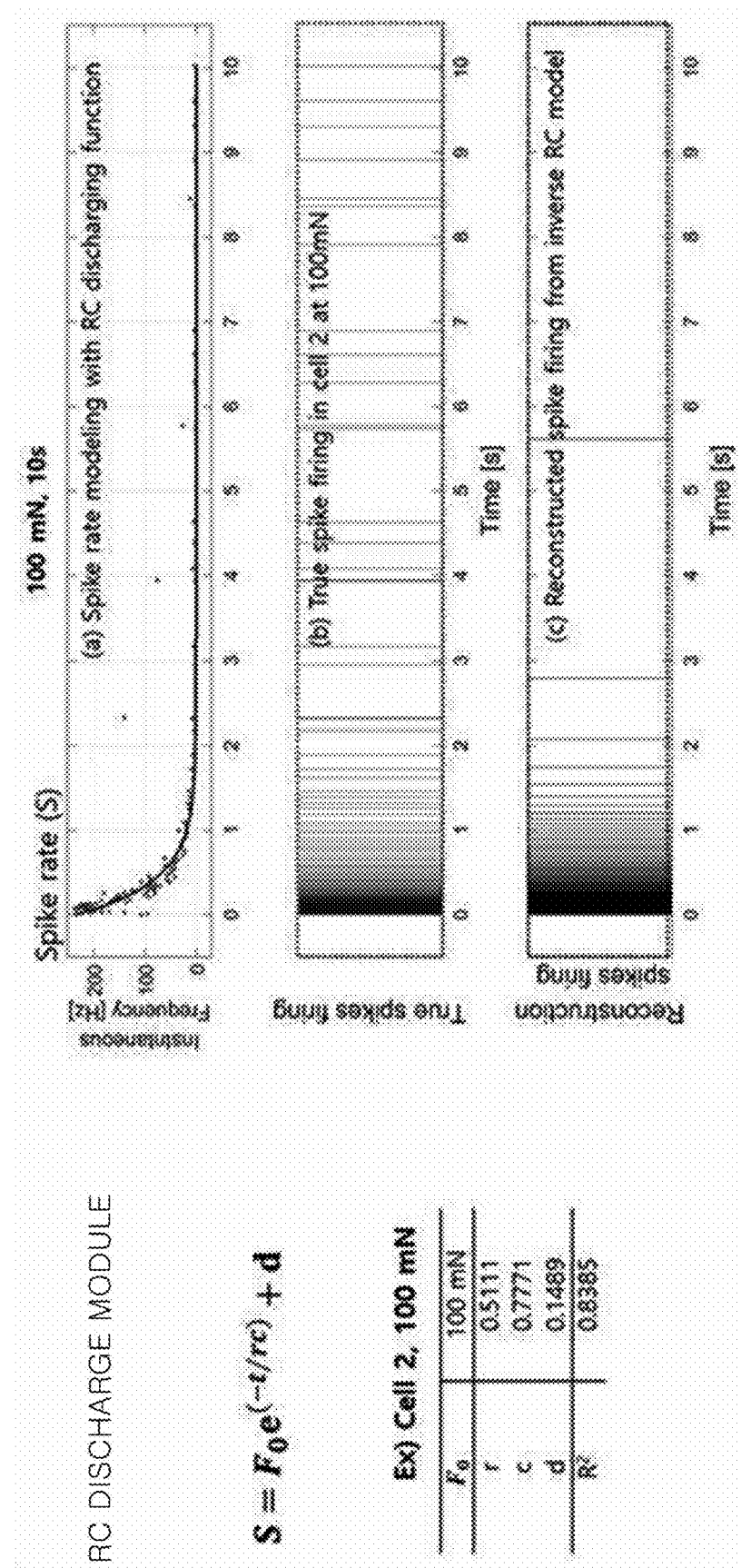
FIG. 2B is a diagram illustrating nerve signal fire spike pattern modeling using a resistance-capacitance (RC) model according to an embodiment of the present disclosure.

FIG. 2B is a diagram illustrating nerve signal spike pattern modeling using an RC model according to an embodiment of the present disclosure.

As illustrated in FIG. 2B, when force is applied, the obtained nerve spike rate is displayed over time and modeled using an RC discharging function to obtain parameters as shown in Equation 3 and Table 1 below. Here, a similarity rate $R^2$ of the model is 0.84, and thus a very accurate model may be obtained.

$$S = F_0 e^{(-t/rc)} + d \qquad \text{[Equation 3]}$$

TABLE 1

| Ex) Cell 2, 100 mN | |
|---|---|
| $F_0$ | 100 ml |
| r | 0.5111 |
| c | 0.7771 |
| d | 0.1489 |
| $R^2$ | 0.8385 |

As illustrated in FIG. 2B, a nerve spike pattern may be obtained by inducing a spike pattern using an RC discharging model. A nerve spike pattern very similar to the actual nerve spike pattern is obtained.

In particular, in this experiment, from 0 to 3 seconds, the nerve spike pattern matches the actual spike pattern by 90% or more, and after 3 seconds, the experimental results evaluate that the obtained RC model is very accurate when considering the noise in the experiment.

Figure 3:
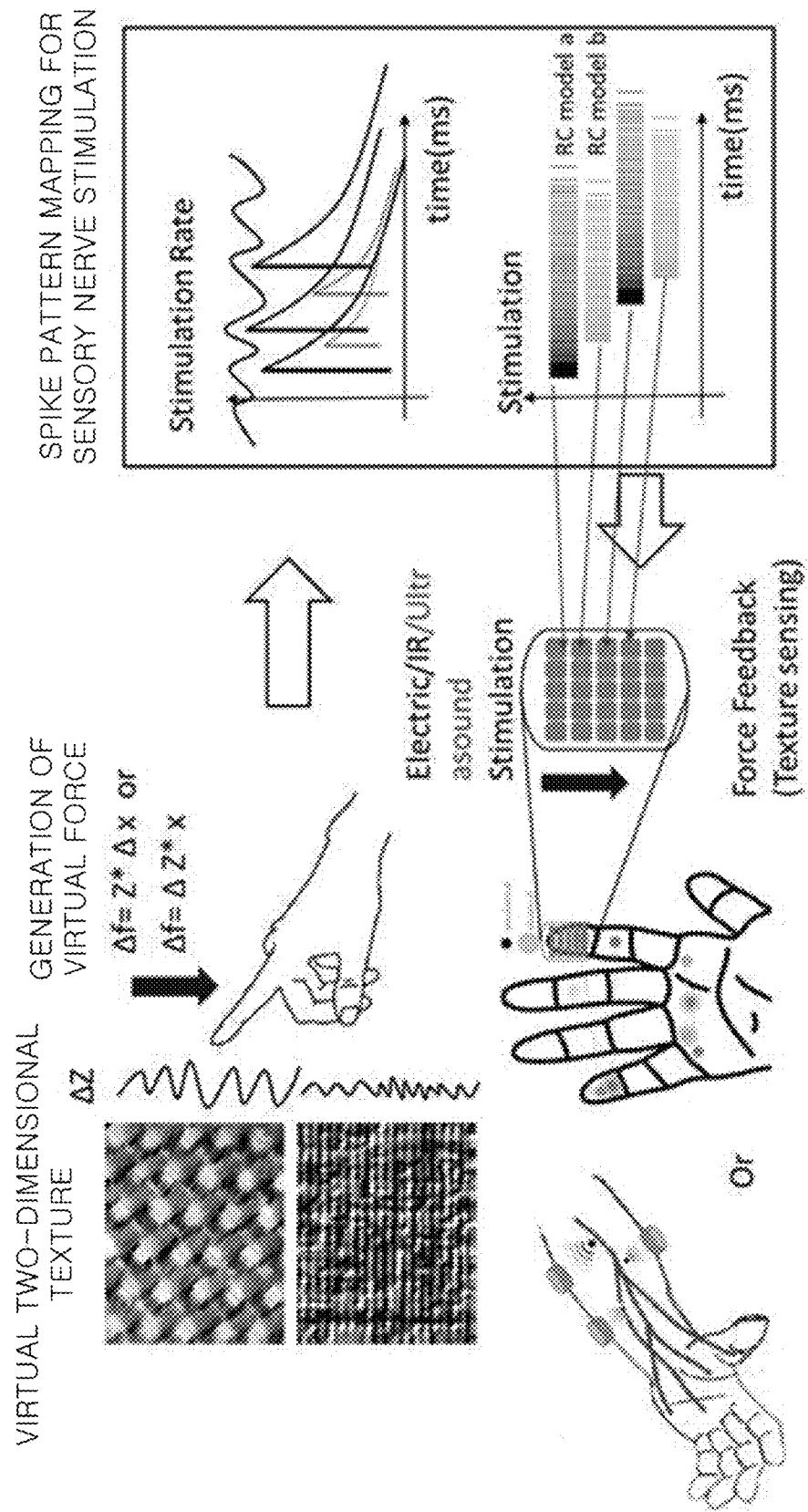
FIG. 3 is a diagram illustrating a method of realizing a virtual 2D texture according to an embodiment of the present disclosure.

FIG. 3 is a diagram illustrating a method of realizing a virtual 2D texture according to an embodiment of the present disclosure.

Referring to FIG. 3, in order to generate virtual force through an impedance of an object in a virtual space and to allow a nerve to feel the virtual force, a technology of forming a nerve stimulation pattern and stimulating the formed nerve stimulation pattern with electricity, light, and ultrasonic waves so that it feels the virtual force and a method of realizing a virtual two-dimensional texture are disclosed.

Since the impedance was previously assigned to the object as the method of obtaining virtual force, virtual force for a horizontal motion is obtained through the change in the impedance of the object over time as shown in Equation 4. In this case, the virtual force is obtained, but the force corresponding to the impedance changing over time is obtained.

$$\Delta f = \Delta Z^* x \quad \text{[Equation 4]}$$

When the spike pattern according to each time is modeled using the previous RC model for the obtained virtual force, and the modeled spike pattern is sequentially transmitted to the two-dimensional stimulation device, a user may directly feel the texture implemented in the virtual space.

According to the present disclosure, each of the values of the force obtained in the virtual space may be obtained using the RC model, and the values may be implemented again in temporal order, and when a temporal nerve spike rate is represented by the sum of several models for one nerve signal, it is very effective in expressing the texture.

The present patent discloses a method of obtaining a nerve spike rate by overlapping these several models.

Figure 4A:
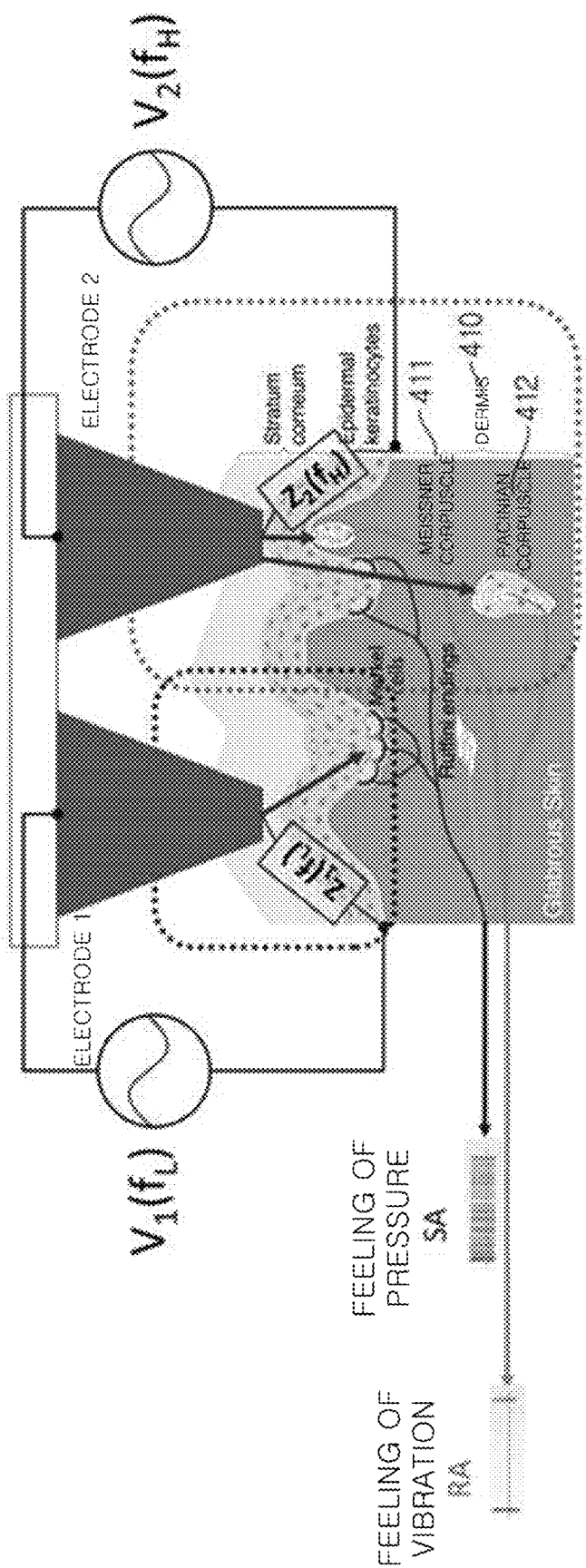
FIG. 4A is a diagram illustrating a method of using a difference in bioelectrical impedance according to an electrical signal frequency according to an embodiment of the present disclosure.

FIG. 4A is a diagram illustrating a method of using a difference in bioelectrical impedance according to a frequency of an electrical signal according to an embodiment of the present disclosure.

Referring to FIG. 4A, a tactile nerve stimulation unit, which can be worn on or attached to a finger and used, is composed of a two-dimensional electrode array, and individual electrical signals are applied from each electrode, but the bioelectrical impedance varies according to the frequency of the electrical signal.

In the case of a low frequency $f_L$ of hundreds of hertz or less, since a bioelectrical impedance $Z_1(f_L)$ is large, a depth at which electrical stimulation may be made at the same voltage is low, and thus Merkel discs distributed in the epidermis are mainly stimulated, and a user may feel the change in pressure.

In the case of a high frequency $f_H$ of thousands of hertz or more, since a bioelectrical impedance $Z_2(f_H)$ is small, a depth at which the electrical stimulation may be made at the same voltage is deep, and thus Meissner corpuscles 411 or Pacinian corpuscles 412 distributed in the dermis 410 are stimulated, and a user may feel a feeling of vibration.

Figure 4B:
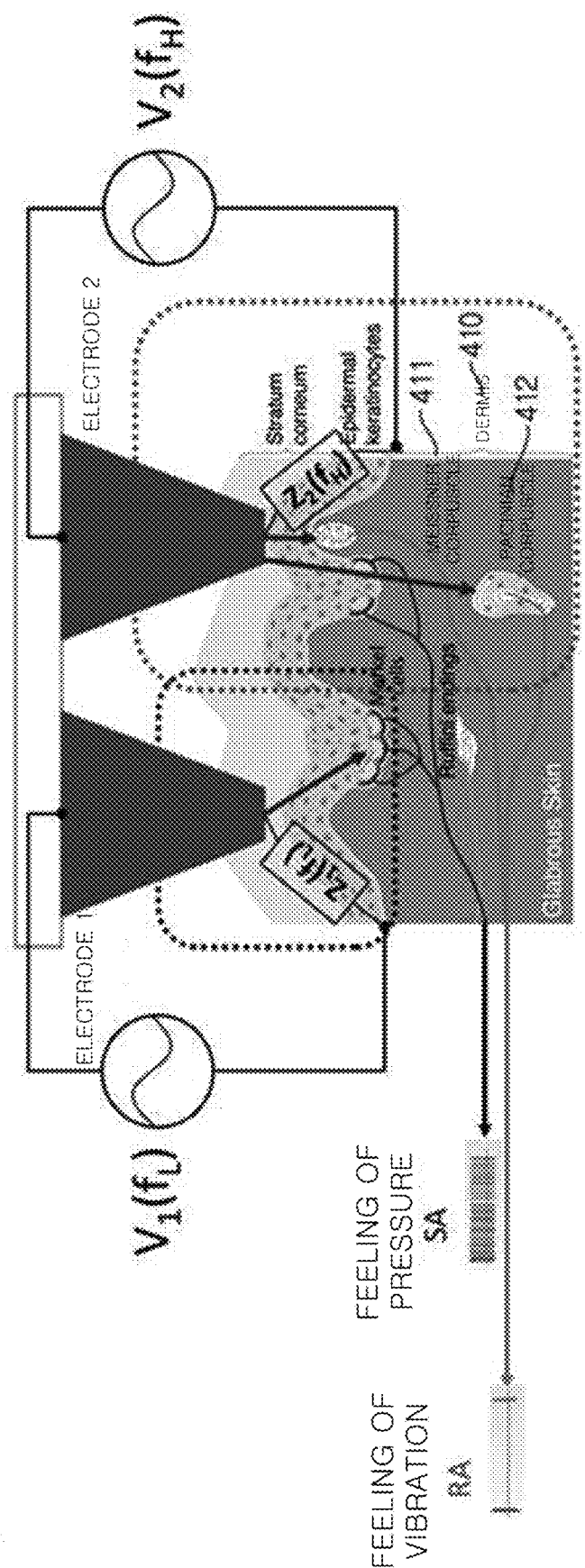
FIG. 4B is a diagram illustrating a method of adjusting a width and length of an individual electrode and using an impedance matching film on an electrode surface according to an embodiment of the present disclosure.

FIG. 4B is a diagram illustrating a method of adjusting a width and length of an individual electrode and using an impedance matching film on an electrode surface according to an embodiment of the present disclosure.

Referring to FIG. 4B, the depth to which the electrical stimulation is applied may be varied by changing the width and length of the individual electrode of the two-dimensional electrode array or by coating the impedance matching film 420 to change the bioelectrical impedance.

In general, a stratum corneum, which is an outermost area of the epidermis, has a thickness of tens to hundreds of micrometers, and when the width of the two-dimensional electrode array is made smaller and the depth of the two-dimensional electrode array is made larger than the stratum corneum, since the bioelectrical impedance may be greatly reduced without damaging the skin, it is possible to feel a tactile sensation with electrical stimulation of several volts.

When the width and length of the electrode are properly adjusted, since the Merkel disc s distributed in the epidermis may be mainly electrically stimulated, or the Meissner corpuscles 411 distributed in the dermis 410 or the Pacinian corpuscles 412 deep in the skin may be electrically stimulated, the control may be performed so that some electrodes may electrically stimulate the Merkel discs to give a feeling of pressure and some electrodes may electrically stimulate the Meissner corpuscles 411 or the Pacinian corpuscles 412 so that slow vibrations or fast and strong vibrations are felt, respectively.

When the impedance matching film 420 is applied on the electrode surface, the bioelectrical impedance may be more easily adjusted, which may facilitate the selective electrical stimulation of the tactile sensory receptor.

Figure 5A:
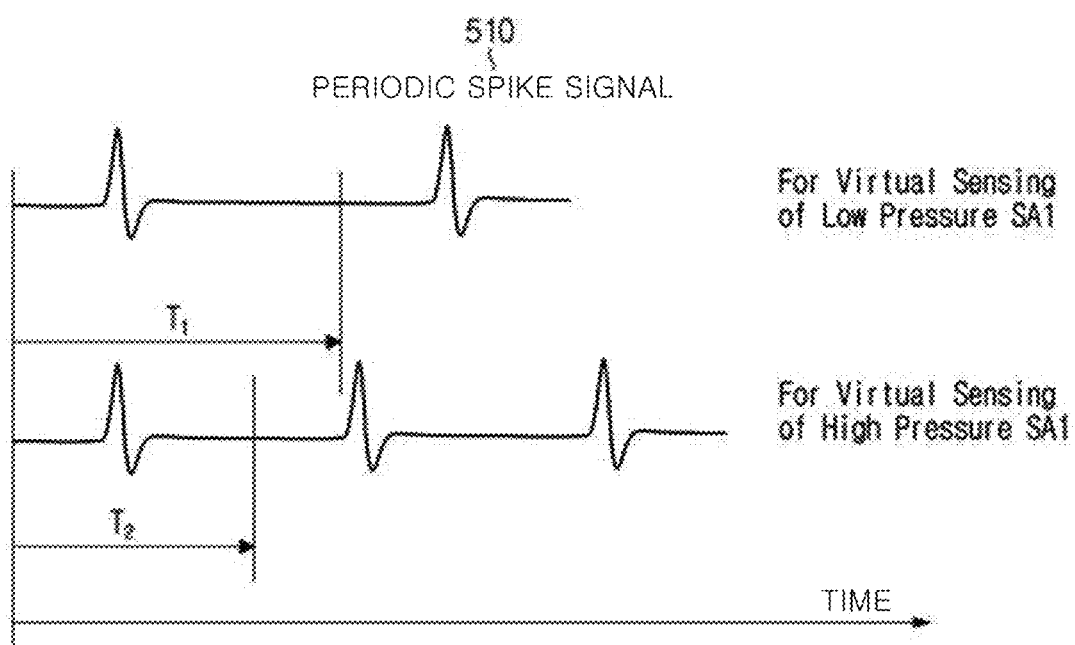
FIG. 5A is a diagram illustrating a method of electrically stimulating a Merkel disc, which is a slow adapting (SA1) tactile sensory receptor that detects pressure, according to an embodiment of the present disclosure.

FIG. 5A is a diagram illustrating a method of electrically stimulating a Merkel disc, which is an SA1 tactile sensory receptor that detects pressure, according to an embodiment of the present disclosure.

FIG. 5A illustrates an example of using a pattern of an electrical signal, which stimulates a tactile sensory nerve receptor by applying a periodic spike signal 510 so that a tactile sensation such as a feeling of pressure is felt.

As a method of electrically stimulating a Merkel disc, which is the SA1 tactile sensory receptor detecting low pressure, the periodic spike signal 510 is applied, but a relatively long signal period $T_1$ may be used to for a low pressure to be felt and a relatively short signal period $T_2$ may be used for a low feeling of pressure.

Figure 5B:
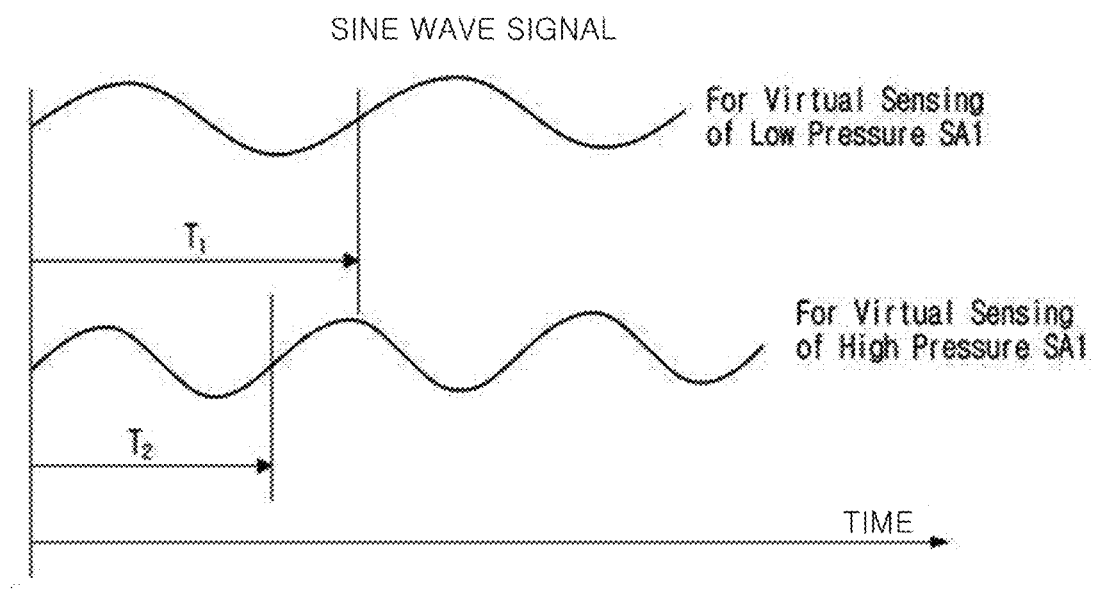
FIG. 5B is a diagram illustrating a method of electrically stimulating a Merkel disc, which is the SA1 tactile sensory receptor that detects pressure, according to an embodiment of the present disclosure.

FIG. 5B is a diagram illustrating a method of electrically stimulating a Merkel disc, which is an SA1 tactile sensory receptor that detects pressure, according to an embodiment of the present disclosure.

FIG. 5B illustrates an example of using a pattern of an electrical signal to convey a tactile sensation such as a feeling of pressure by applying a sine wave signal to simulate a tactile sensory nerve receptor as another embodiment of the present invention.

As a method of electrically stimulating a Merkel disc which is an SA1 tactile sensory receptor that detects pressure, an electrical signal of a sine wave is applied, but a relatively long signal period $T_1$ may be used for a low pressure to be felt. A higher feeling of pressure may be felt when a relatively short signal period $T_2$ is used. Here, the magnitude of $T_1$ exceeds $T_2$.

Figure 6A:
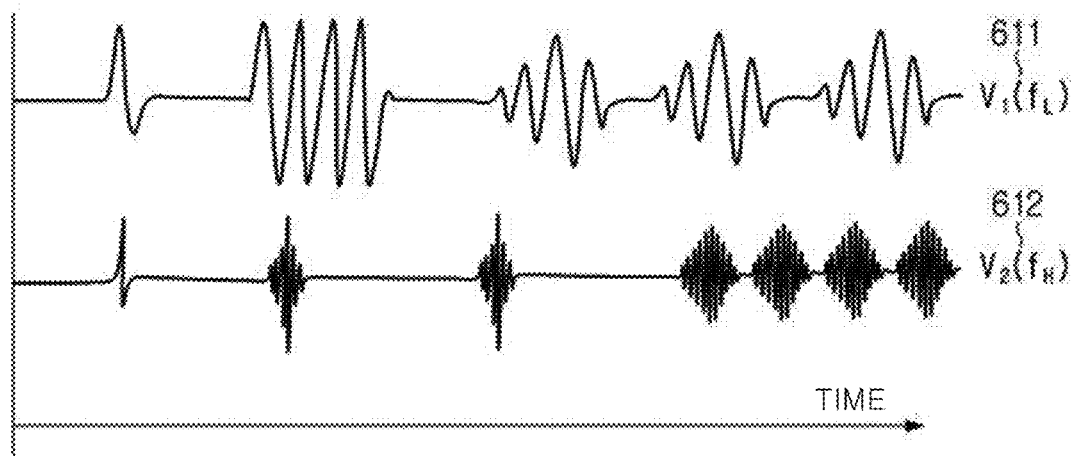
FIG. 6A is a diagram illustrating a method of electrically stimulating a Merkel disc, which is the SA1 tactile sensory receptor that detects pressure, according to an embodiment of the present disclosure.

FIG. 6A is a diagram illustrating a method of electrically stimulating a Merkel disc, which is an SA1 tactile sensory receptor that detects pressure, according to an embodiment of the present disclosure.

Referring to FIG. 6A, in an upper portion 611 of FIG. 6A, the electrical stimulation is applied using a single spike signal in $V_1(f_L)$, which is a voltage signal having a low frequency $f_L$ as a carrier frequency, as the electrical signal corresponding to the embodiment of FIG. 4A as well as various signals such as a sine wave signal, a short time pulse signal, and a frequency modulation signal. An example of the method of applying electrical stimulation to Merkel discs distributed in an epidermis to convey a feeling of pressure due to a high bioelectrical impedance $Z_1(f_L)$ is shown.

In addition, in a lower portion 612 of FIG. 6A, various signals such as a pulse signal having a short time width or a frequency modulated signal as well as a single spike signal are used in $V_2(f_H)$, which is a voltage signal having a high frequency $f_H$ as a carrier frequency. An example of the method of applying electrical stimulation to Meissner corpuscles and Pacinian corpuscles distributed in the dermis to convey a feeling of vibration due to a low bioelectrical impedance $Z_1(f_L)$ is shown.

Figure 6B:
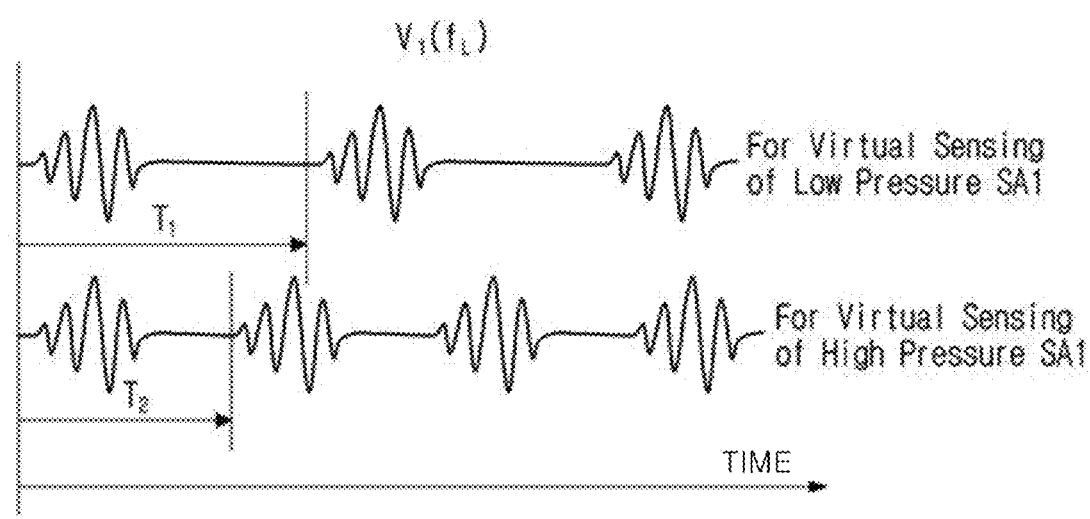
FIG. 6B is a diagram illustrating a method of electrically stimulating a Merkel disc, which is the SA1 tactile sensory receptor that detects pressure, according to an embodiment of the present disclosure.

FIG. 6B is a diagram illustrating a method of electrically stimulating a Merkel disc, which is an SA1 tactile sensory receptor that detects pressure, according to an embodiment of the present disclosure.

Referring to FIG. 6B, as the method of electrically stimulating a Merkel disc, which is an SA1 tactile sensory receptor that detects pressure, a low frequency $f_L$ of several hundred Hz or less is used as the carrier frequency.

FIG. 6B illustrates the method of using a pulse signal having a short time width as well as a spike signal as illustrated in FIG. 5A and applying a periodic pulse signal but using a relatively long signal period $T_1$ so that a low pressure is felt, and by using a relatively short signal period $T_2$, a user may feel a higher pressure.

When selectively stimulated using periodic pulse signals corresponding to a period of electrical spike signals transmitted through nerve neurons of the Meissner corpuscle, a user may feel a slow feeling of vibration. When periodic pulse signals that match a period of electrical spike signals transmitted through nerve neurons of the Pacinian corpuscle are used, a user may feel a fast feeling of vibration.

Figure 6C:
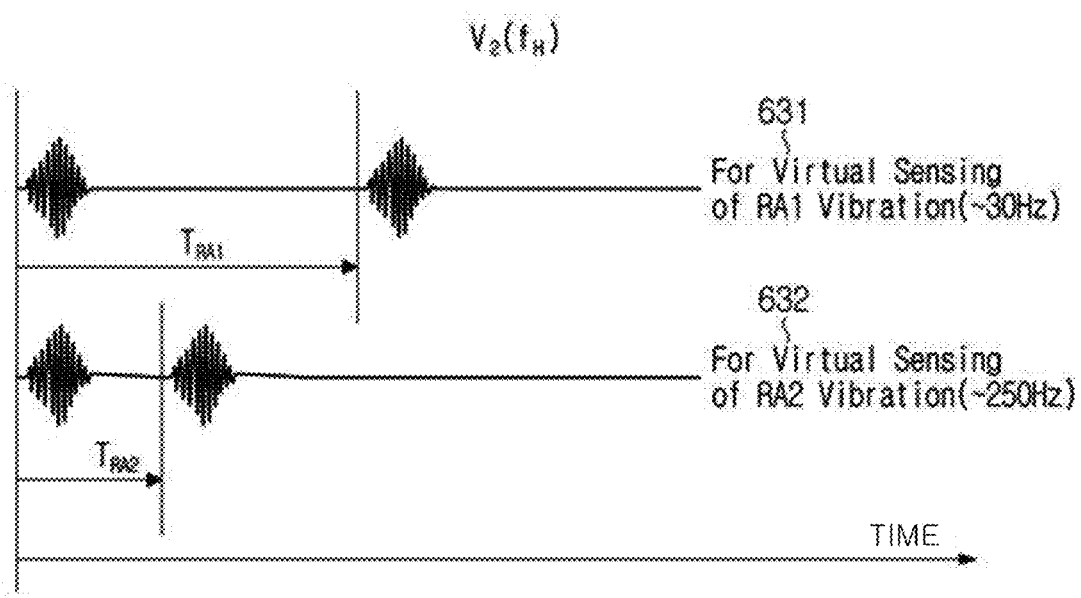
FIG. 6C is a diagram illustrating a method of electrically stimulating a Meissner corpuscle, which is a tactile sensory receptor, and a Pacinian corpuscle, which is a tactile sensory receptor, according to an embodiment of the present disclosure.

FIG. 6C is a diagram illustrating a method of electrically stimulating a Meissner corpuscle, which is a tactile sensory receptor, and a Pacinian corpuscle, which is a tactile sensory receptor, according to an embodiment of the present disclosure.

FIG. 6C illustrates a method of electrically stimulating a Meissner corpuscle 631, which is an RA1 tactile sensory receptor that detects slow vibrations of around 30 Hz, and a Pacinian corpuscle 632, which is an RA2 tactile sensory receptor that detects fast vibrations of around 250 Hz.

Referring to FIG. 6C, a high frequency $f_H$ of several kHz or more is used as a carrier frequency, but a pulse signal having a short time width is used and a relatively long signal period $T_{RA1}$ is used so that a user may feel a slow feeling of vibration. By using a relatively short signal period $T_{RA2}$, a user may feel a faster feeling of vibration.

Figure 7:
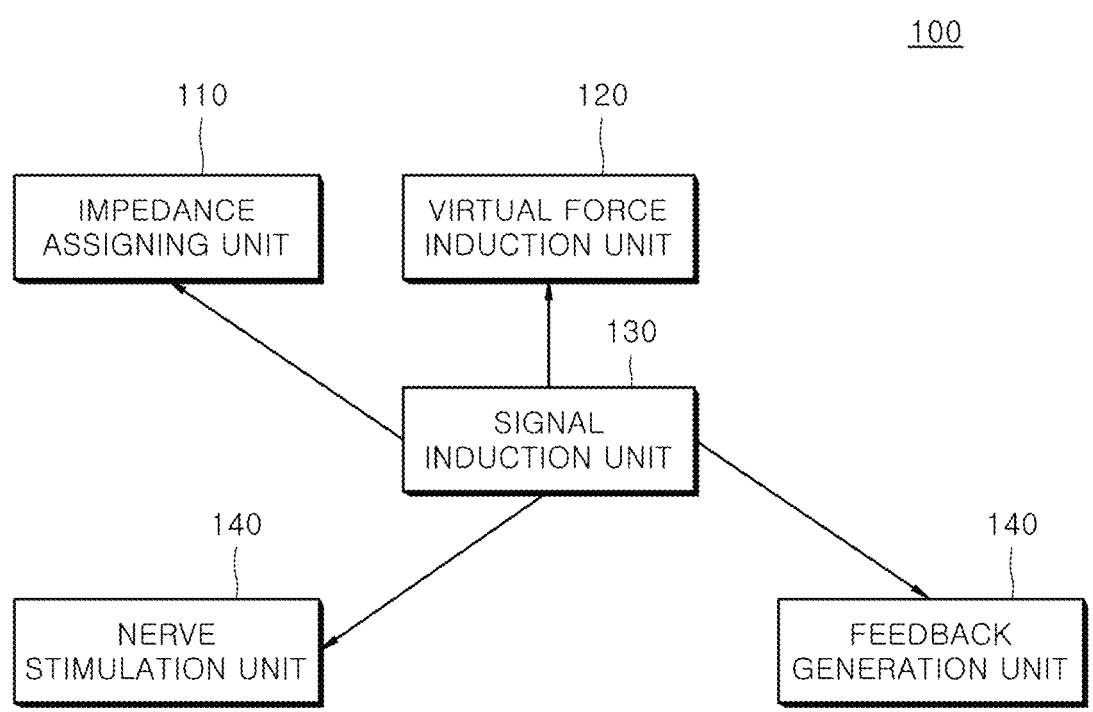
FIG. 7 is a diagram illustrating a configuration of a tactile stimulation device according to an embodiment of the present disclosure.

FIG. 7 is a diagram illustrating a configuration of a tactile stimulation device according to an embodiment of the present disclosure.

Referring to FIG. 7, a tactile stimulation device 100 includes an impedance assigning unit 110, a virtual force induction unit 120, a signal induction unit 130, a nerve stimulation unit 140, and a feedback generation unit 150.

The impedance assigning unit 110 assigns an impedance value to each object in a virtual space.

The virtual force induction unit 120 induces virtual force using displacement between the object and a user's body in the virtual space.

The signal induction unit 130 induces a signal that causes a signal of a sensory nerve to be fired with a value corresponding to the virtual force.

The nerve stimulation unit 140 stimulates a location where a sensory nerve is located temporarily or over time.

The feedback generation unit 150 generates feedback in the virtual space based on the stimulation result.

The impedance assigning unit 110 assigns a representative impedance value differently according to contact strength of the object in the virtual space.

Here, the spike signal is generated by acquiring spike pattern data acquired from the sensory nerve by applying a mechanical force, and using a spike signal of a correlation function based on the acquired spike pattern data.

Here, the correlation functions may include a functions that model resistance-capacity (RC) discharging responses.

The nerve stimulation unit 140 stimulates a nerve by applying any one of electrical signals including a constant magnitude of current, a spike, and a pulse pattern that fire the nerve.

The nerve stimulation unit 140 stimulates a stimulation array corresponding to the individual sensory nerve with the spike according to the movement of the body in the virtual space so that the feedback is felt in the virtual space.

The nerve stimulation unit 140 applies an individual electrical signal from an individual electrode, adjusts a bioelectrical impedance between the individual electrode and the skin manipulation, adjusts a depth at which an electrical spike or a pulse signal may be applied from a skin surface based on the adjusted bioelectrical impedance, and distinguishes tactile sensory nerve receptors based on the adjusted depth, thereby performing stimulation so that the feedback is felt.

The nerve stimulation unit 140 adjusts a frequency of an electrical signal to adjust the bioelectrical impedance between the individual electrode and the skin manipulation.

The nerve stimulation unit 140 adjusts the bioelectrical impedance between the individual electrode and the skin manipulation by changing at least one of the width and length of the individual electrode.

Figure 8:
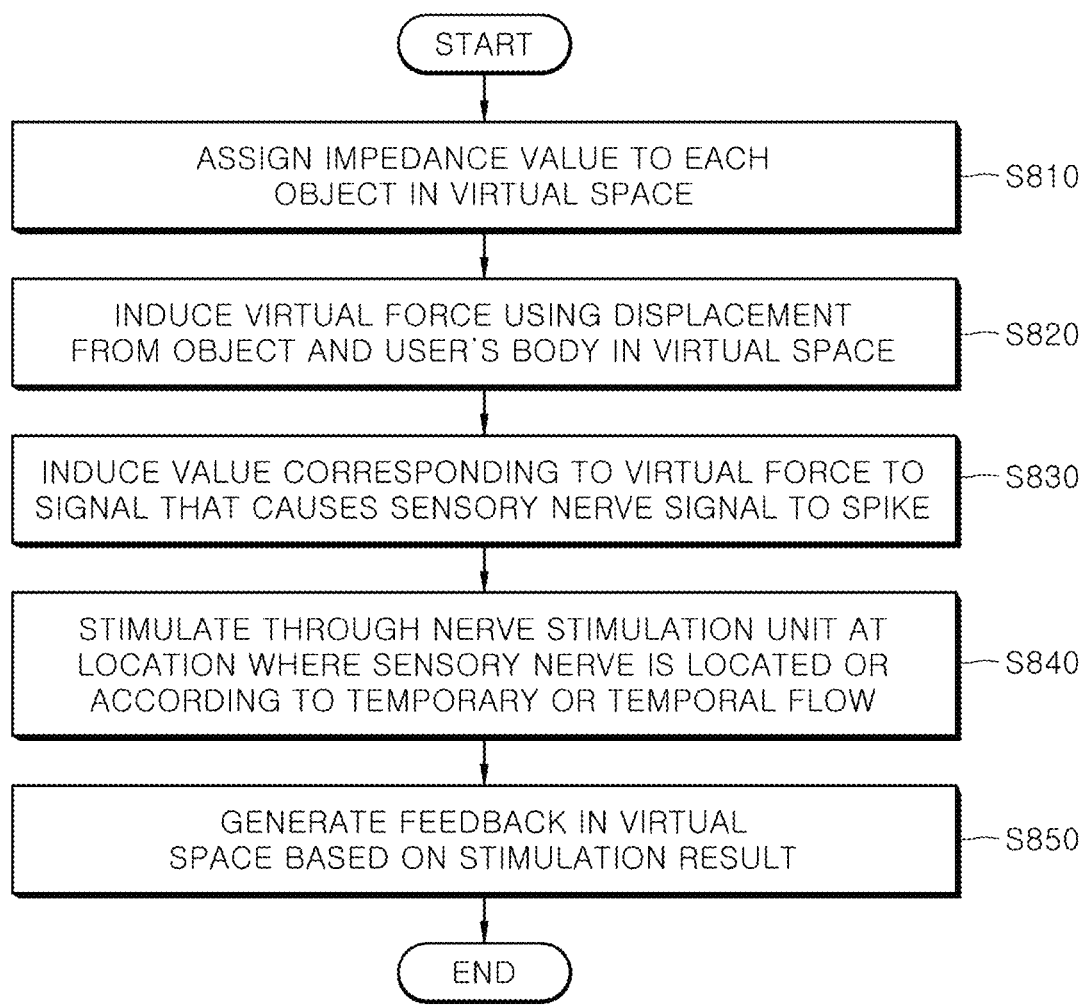
FIG. 8 is a diagram illustrating a configuration of a tactile stimulation method according to an embodiment of the present disclosure.

FIG. 8 is a diagram illustrating a configuration of a tactile stimulation method according to an embodiment of the present disclosure. The present invention is performed by the tactile stimulation device 100.

Referring to FIG. 8, an impedance value is assigned to each object in the virtual space (S810).

The virtual force is derived using the displacement between the object and the user's body in the virtual space (S820).

The value corresponding to the virtual force induces a signal that causes the signal of the sensory nerve to be fired (S830). Here, the signal includes a spike signal or a pulse signal.

The location where the sensory nerve is located is stimulated through the nerve stimulation unit temporarily or over time (S840).

The feedback in the virtual space is generated based on the stimulation result (S850).

Figure 9:
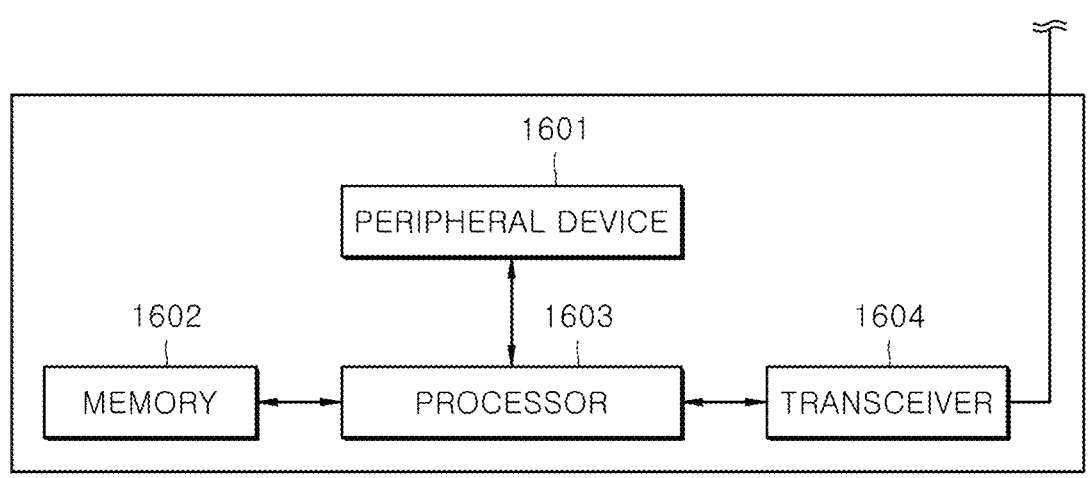
FIG. 9 is a diagram illustrating the configuration of the tactile stimulation device according to the embodiment of the present disclosure.

FIG. 9 is a diagram illustrating the configuration of the tactile stimulation device according to the embodiment of the present disclosure.

Referring to FIG. 9, the tactile stimulation device includes a device 1600. The device 1600 may include a memory 1602, a processor 1603, a transceiver 1604, and a peripheral device 1601. Also, as an example, the device 1600 may further include other components, and is not limited to the above-described embodiment. In this case, as an example, the device may be a device that operates based on the above-described tactile stimulation device.

More specifically, the device 1600 of FIG. 9 may be the tactile stimulation device and exemplary hardware/software architecture. In this case, for example, the memory 1602 may be a non-removable memory or a removable memory. In addition, as an example, the peripheral device 1601 may include a display, GPS, or other peripheral devices, and is not limited to the above-described embodiment.

Also, as an example, the above-described device 1600 may include a communication circuit like the transceiver 1604, and may perform communication with an external device based on the communication circuit.

In addition, as an example, the processor 1603 may include at least one of a general purpose processor, a digital signal processor (DSP), a DSP core, a controller, a microcontroller, application specific integrated circuits (ASICs), field programmable gate array (FPGA) circuits, any other type of integrated circuit (IC) and one or more microprocessors associated with a state machine. That is, the above-described device 1600 may have a hardware/software configuration that performs a control role for controlling the device 1600 described above.

In this case, the processor 1603 may execute computer executable instructions stored in the memory 1602 to perform various essential functions of the tactile stimulation device. For example, the processor 1603 may control at least one of signal coding, data processing, power control, input/output processing, and communication operations. In addition, the processor 1603 may control a physical layer, a MAC layer, and an application layer. In addition, as an example, the processor 1603 may perform authentication and security procedures in an access layer and/or an application layer, and the like, and is not limited to the above-described embodiment.

For example, the processor 1603 may communicate with other devices through the transceiver 1604. For example, the processor 1603 may control an emotion recognition device to communicate with other devices through a network through execution of computer executable instructions. That is, the communication performed in the present disclosure may be controlled. For example, the transceiver 1604 may transmit an RF signal through an antenna and may transmit the signal based on various communication networks.

In addition, as an example, multiple-input and multiple-output (MIMO) technology, beamforming, and the like may be applied as an antenna technology, which is not limited to the above-described embodiment. In addition, the signal transceived through the transceiver 1604 may be modulated and demodulated and controlled by the processor 1603, and is not limited to the above-described embodiment.

Various embodiments of the present disclosure are intended to explain representative aspects of the present disclosure, rather than listing all possible combinations, and matters described in various embodiments may be applied independently or in combinations of two or more.

In addition, various embodiments of the present disclosure may be implemented by hardware, firmware, software, or a combination thereof, or the like. For implementation by hardware, various embodiments of the present disclosure may be implemented by one or more ASICs, DSPs, digital signal processing devices (DSPDs), programmable logic devices (PLDs), FPGAs, processors, controllers, microcontrollers, microprocessors, or the like. For example, it is obvious that it may be implemented in the form of a program stored in a non-transitory computer readable medium that may be used at the end or edge, or in the form of a program stored in a non-transitory computer readable medium that may be used at the edge or in the cloud. In addition, it may be implemented with a combination of various hardware and software components.

The scope of the present disclosure includes software or machine-executable instructions (e.g., operating systems, applications, firmware, programs, etc.) that cause operations according to the methods of various embodiments to be executed on a device or computer, and a non-transitory computer-readable medium in which such software, instructions, etc., are stored and executable on a device or computer.

According to an embodiment of the present disclosure, compared to the related art, a spike or pulse pattern mapping method for sensory nerve stimulation can be implemented based on a method of obtaining virtual force by assigning an impedance to a virtual object in a virtual space to directly stimulate nerves, so that the force obtained from the virtual space can be more directly implemented, thereby improving user convenience.

According to an embodiment of the present disclosure, values of force obtained in a virtual space can be obtained using an RC model, and the values can be implemented again in temporal order, and when a temporal nerve spike rate is represented by the sum of several models for one nerve signal, it is very effective in expressing a texture.

According to one embodiment of the present disclosure, since nerve spike rate patterns are obtained for various sizes of forces, and the acquired nerve spike rate patterns are stimulated with electricity, ultrasonic waves, and light, it is possible to express the virtual force in detail.

According to an embodiment of the present disclosure, since sensory nerves can be stimulated using a value obtained by overlapping a nerve spike rate over time with respect to a two-dimensional texture, it is possible to precisely implement the two-dimensional texture.

Effects which can be achieved by the present disclosure are not limited to the above-described effects. That is, other objects that are not described may be obviously understood by those skilled in the art to which the present disclosure pertains from the above detailed description.

Since various substitutions, modifications, and alterations may be applied to the present disclosure described hereinabove by those skilled in the art to which the present disclosure pertains without departing from the scope and spirit of the present disclosure, the scope of the present disclosure is not limited to the above-described exemplary embodiments or the accompanying drawings.

What is claimed is:

1. A tactile stimulation method comprising:
   assigning an impedance value to each object in a virtual space;
   inducing virtual force using the impedance value assigned to the object and displacement between the object and a user's body in the virtual space;
   inducing a nerve spike pattern for sensory nerve stimulation in order to implement the induced virtual force;

stimulating a location where the sensory nerve is located by applying an electrical signal according to the induced nerve spike pattern through a nerve stimulation unit temporarily or over time; and generating feedback in the virtual space based on a stimulation result, wherein the nerve spike pattern is derived based on a resistance-capacity (RC) model which is predefined based on intervals between spike signals fired by a plurality of sensory receptors when a mechanical stimulation is applied to skin layer in which tactile nerves are distributed.

2. The tactile stimulation method of claim 1, wherein the assigning of the impedance value to each object in the virtual space includes assigning a different representative impedance value according to contact strength of the object in the virtual space.

3. The tactile stimulation method of claim 1, wherein the correlation functions may include a functions that model resistance-capacity (RC) discharging responses.

4. The tactile stimulation method of claim 1, the electrical signal includes a constant current, a spike, and/or a pulse pattern that fire the nerve.

5. The tactile stimulation method of claim 1, further comprising stimulating a stimulation array corresponding to an individual sensory nerve with a spike according to movement of the body in the virtual space so that the feedback is felt in the virtual space.

6. The tactile stimulation method of claim 1, further comprising:
applying an individual electrical signal from an individual electrode;
adjusting a bioelectrical impedance between the individual electrode and skin manipulation;
adjusting a depth at which the electrical signal is applied on a skin surface based on the adjusted bioelectrical impedance; and
performing stimulation so that the feedback is felt by distinguishing a tactile sensory nerve receptor based on the adjusted depth.

7. The tactile stimulation method of claim 6, further comprising adjusting a frequency of the electrical signal to adjust the bioelectrical impedance between the individual electrode and the skin manipulation.

8. The tactile stimulation method of claim 6, further comprising adjusting the bioelectrical impedance between the individual electrode and the skin manipulation by changing at least one of a width and a length of the individual electrode.

9. The tactile stimulation method of claim 6, further comprising adjusting the bioelectrical impedance between the individual electrode and the skin manipulation using an impedance matching film applied on the individual electrode.

10. A tactile stimulation device comprising:
an impedance assigning unit configured to assign an impedance value to each object in a virtual space;
a virtual force induction unit configured to induce virtual force using the impedance value assigned to the object and displacement between the object and a user's body in the virtual space;
a signal induction unit configured to induce a signal a nerve spike pattern for sensory nerve stimulation in order to implement the induced virtual force;
a nerve stimulation unit configured to stimulate a location where the sensory nerve is located by applying an electrical signal according to the induced nerve spike pattern temporarily or over time; and
a feedback generation unit configured to generate feedback in the virtual space based on a stimulation result,
wherein the nerve spike pattern is derived based on a resistance-capacity (RC) model which is predefined based on intervals between spike signals fired by a plurality of sensory receptors when a mechanical stimulation is applied to skin layer in which tactile nerves are distributed.

11. The tactile stimulation device of claim 10, wherein the impedance assigning unit assigns a representative impedance value differently according to contact strength of the object in the virtual space.

12. The tactile stimulation device of claim 10, wherein the correlation functions may include a functions that model resistance-capacity (RC) discharging responses.

13. The tactile stimulation device of claim 10, wherein the nerve stimulation unit stimulates the nerve by applying the electrical signals including a constant current, a spike, and/or a pulse pattern that fire the nerve.

14. The tactile stimulation device of claim 10, wherein the nerve stimulation unit stimulates a stimulation array corresponding to an individual sensory nerve with a spike according to movement of the body in the virtual space so that the feedback is felt in the virtual space.

15. The tactile stimulation device of claim 10, wherein the nerve stimulation unit applies an individual electrical signal from an individual electrode,
adjusts a bioelectrical impedance between the individual electrode and skin manipulation,
adjusts a depth at which the electrical signal is applied on a skin surface based on the adjusted bioelectrical impedance, and
performs stimulation so that the feedback is felt by distinguishing a tactile sensory nerve receptor based on the adjusted depth.

16. The tactile stimulation device of claim 15, wherein the nerve stimulation unit adjusts a frequency of the electrical signal to adjust the bioelectrical impedance between the individual electrode and the skin manipulation.

17. The tactile stimulation device of claim 15, wherein the nerve stimulation unit adjusts the bioelectrical impedance between the individual electrode and the skin manipulation by changing at least one of a width and a length of the individual electrode.

18. A tactile stimulus recognition device comprising:
a transceiver configured to transmit and receive data to and from an external device; and
a processor configured to:
assign an impedance value to each object in a virtual space through the transceiver;
induce virtual force using the impedance value assigned to the object and displacement between the object and a user's body in the virtual space;
induce a nerve spike pattern for sensory nerve stimulation in order to implement the induced virtual force;
stimulate a location where the sensory nerve is located by applying an electrical signal according to the induced nerve spike pattern temporarily or over time; and
generate the feedback in the virtual space based on a stimulation result,
wherein the nerve spike pattern is derived based on a resistance-capacity (RC) model which is predefined based on intervals between spike signals fired by a plurality of sensory receptors when a mechanical stimulation is applied to skin layer in which tactile nerves are distributed.

* * * * *